(12) United States Patent
Kubo et al.

(10) Patent No.: US 7,273,953 B2
(45) Date of Patent: Sep. 25, 2007

(54) PROCESS FOR PRODUCING ARYLAMINE

(75) Inventors: Shinji Kubo, Hiratsuka (JP); Taichi Shintou, Hiratsuka (JP); Hidenori Aoki, Hiratsuka (JP)

(73) Assignee: Fujifilm Finechemicals Co., Ltd., Tokyo (JP)

( * ) Notice: Subject to any disclaimer, the term of this patent is extended or adjusted under 35 U.S.C. 154(b) by 283 days.

(21) Appl. No.: 10/527,064

(22) PCT Filed: Sep. 9, 2003

(86) PCT No.: PCT/JP03/11510

§ 371 (c)(1),
(2), (4) Date: Mar. 9, 2005

(87) PCT Pub. No.: WO2004/024670

PCT Pub. Date: Mar. 25, 2004

(65) Prior Publication Data

US 2006/0069287 A1 Mar. 30, 2006

(30) Foreign Application Priority Data

Sep. 10, 2002 (JP) .............................. 2002-264202

(51) Int. Cl.
*C07C 209/10* (2006.01)
(52) U.S. Cl. ..................................................... 564/405

(58) Field of Classification Search ..................... None
See application file for complete search history.

(56) References Cited

U.S. PATENT DOCUMENTS

| 4,404,400 A | 9/1983 | Heise et al. |
| 6,043,370 A | 3/2000 | Kubo et al. |

FOREIGN PATENT DOCUMENTS

| JP | 57-40445 A | 3/1982 |
| JP | 62-283953 A | 12/1987 |

OTHER PUBLICATIONS

Database CAPLUS on STN, Acc. No. 2000:612055, Suzuka et al., JP 2000239235 (Sep. 5, 2000) (abstract).*

* cited by examiner

*Primary Examiner*—Brian Davis
(74) *Attorney, Agent, or Firm*—Sughrue-Mion, PLLC

(57) ABSTRACT

A process for producing an arylamine is provided which is characterized by reacting an aromatic halogen compound with an aromatic amine in the presence of an organic salt selected from specific pyridinium salts, imidazolium salts and quaternary onium salts, a copper catalyst, and a base. Thus, the reaction of even an aromatic halogen compound substituted by an electron-donating group proceeds efficiently, and an inexpensive chlorinated aromatic compound or brominated aromatic compound is usable, and an arylamine, in particular a triarylamine or diarylamine, having a high purity can be produced at low cost.

10 Claims, 5 Drawing Sheets

PROCESS FOR PRODUCING ARYLAMINE

CROSS-REFERENCE TO RELATED APPLICATIONS

This application is a 371 of Application No. PCT/JP03/11510 filed on Sep. 9, 2003, and claims foreign priority benefit under 35 U.S.C. § 365(b) of JP 2002-264202 filed Sep. 10, 2002. The entire disclosures of the prior applications, application numbers PCT/JP03/11510 and JP 2002-264202, are hereby incorporated by reference.

TECHNICAL FIELD

The present invention provides a process for producing at low cost an arylamine, in particular a triarylamine or diarylamine, which has a high purity and is useful as a raw material for electronic materials or as an intermediate therefor.

BACKGROUND ART

The reaction according to the invention falls under the category of reactions classified as the Ullmann condensation reaction.

The Ullmann condensation reaction is a process in which an aromatic amine is reacted with an aromatic halogen compound, preferably an aromatic iodide, in the presence of a base and a copper catalyst to synthesize an arylamine. It was discovered by F. Ullmann. (See, for example, F. Ullmann, *Chemische Berichte.*, 1920, Vol. 36, p. 2382.)

This reaction has generally required a prolonged reaction time and necessitated a high temperature of usually 200° C. or higher for attaining a practical rate of arylation. Because of this, by-products generate in large amounts as a result of the oxidation, disproportionation, dimerization reaction, etc. of the reaction product. Although raw materials for electronic materials or intermediates therefor are generally required to have a high purity, purification by the removal of these by-products is exceedingly difficult and has posed a serious problem. In addition, there have been drawbacks leading to a cost increase, for example, that the reaction proceeds efficiently only when an iodized aromatic compound, which is more expensive, is used as the aromatic halogen compound to be reacted with an aromatic amine, and that an apparatus usable for the high-temperature reaction is necessary.

Methods for causing the reaction to proceed efficiently and inhibiting the generation of by-products have been attempted. For example, a process for triarylamine production which comprises reacting an aromatic amine compound with an iodized aromatic compound without using a solvent or in an inert hydrocarbon solvent in the presence of a copper catalyst and potassium hydroxide (JP-B-01-29182), processes for triarylamine production in which a surfactant such as a crown ether or polyethylene glycol is added (see JP-A-11-87061, JP-A-2000-178237, JP-A-2000-273068, and JP-A-2000-256276), and the like have been proposed. However, these processes also are not fully satisfactory in purity and the problem concerning the use of an iodized aromatic compound still remains unsolved.

For producing an arylamine compound having a high purity, it is preferred to conduct the reaction at a lower temperature. Processes for producing a triarylamine compound have been proposed which comprise reacting an aromatic amine compound with an iodized aromatic compound in an aromatic solvent in the presence of a copper catalyst, potassium hydroxide, and a tertiary amine compound at 120-150° C. (see JP-A-9-323958, JP-A-9-323959, JP-A-10-212267, JP-A-10-212268, JP-A-10-212269, and JP-A-10-312073). However, these processes also have been unsatisfactory in both yield and purity and necessitated a high degree of purification. Furthermore, in these processes also, it is necessary to use an expensive iodized aromatic compound because use of an inexpensive chlorinated aromatic compound or brominated aromatic compound therein results in a low yield and these compounds are hence unusable. Namely, these processes still have the problem concerning cost.

Furthermore, processes for producing nitrodiphenylamine at low cost from a halogenated nitrobenzene and an aniline derivative in the presence of a copper catalyst and an ammonium salt or phosphonium salt (see JP-A-57-40445) or in the presence of a copper catalyst and a phosphonium salt (see patent document 13) through the Ullmann reaction have been proposed. However, these are specialized processes for obtaining nitrodiphenylamine from a reactive halogenated nitrobenzene and are unsuitable for the synthesis of various arylamines by techniques of organic chemistry. In addition, since the nitrodiphenylamine obtained as the target compound does not have a high purity, these processes are not satisfactory when used for producing at low cost a high-purity arylamine, in particular a triarylamine or diarylamine, which is useful as a raw material for electronic materials or as an intermediate therefor.

Moreover, a process has been proposed in which a chlorinated aromatic compound or brominated aromatic compound is reacted with an aromatic amine compound in an aromatic solvent in the presence of a palladium catalyst, phosphine compound, and base at 20-140° C. (see JP-A-10-139742, JP-A-10-195031, JP-A-10-310561, JP-A-11-5769, *Angewante Chemie. International English ed.*, 1998, Vol. 37, pp. 2046-2047, *J. Am. Chem. Soc.*, 1998, Vol. 120, pp. 9722-9723, *J. Org. Chem.*, 1996, Vol. 61, p. 1133, and *Tetrahedron Letters*, 1995, Vol. 36, No. 21, pp. 3609-3612). However, since palladium compounds are exceedingly expensive, the process proposed is not an industrially advantageous process. The process has been unsatisfactory also in yield and purity.

DISCLOSURE OF THE INVENTION

An object of the invention is to provide a novel process for producing an arylamine, especially a triarylamine or diarylamine, having an exceedingly high purity at low cost, in which even aromatic halogen compounds substituted by an electron-donating group, which have lower reactivity, efficiently undergo the reaction and inexpensive chlorinated aromatic compounds and brominated aromatic compounds can be used.

The object of the invention is accomplished with the processes shown below.

1. A process for producing an arylamine, which comprises reacting an aromatic halogen compound represented by the following general formula (4) or (5) with an aromatic amine in the presence of at least one organic salt represented by the following general formulae (1) to (3), a copper catalyst, and a base:

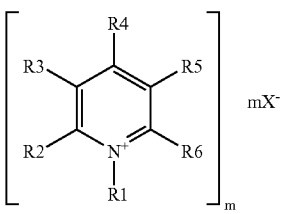

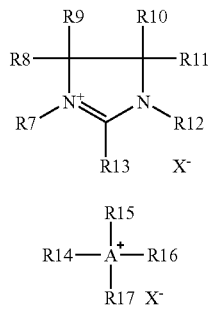

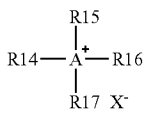

(wherein A represents a nitrogen atom, phosphorus atom, arsenic atom, or antimony atom; R1 to R17 may be the same or different and each represent a hydrogen atom, alkyl group, alkenyl group, alkynyl group, aryl group, hydroxyl group, alkoxy group, aryloxy group, mercapto group, alkylthio group, arylthio group, carbonyl group, sulfonyl group, oxycarbonyl group, carbonyloxy group, nitro group, cyano group, amino group, carbonylamino group, sulfonylamino group, heterocycle residue, or halogen atom, provided that R1, R7, R12, and R14 to R17 each is not a hydrogen atom, that R8 and R10 in cooperation may form a double bond, and that two bondable substituents in R1 to R6 or in R7 to R13 may be bonded to each other to form a ring; m represents 1 or 2; when m is 2, any of R2 to R6 represents a connecting group and the two moieties connected to each other may differ; and $X^-$ represents any anion);

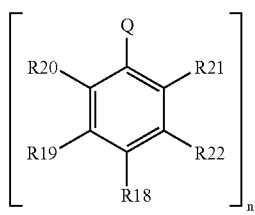

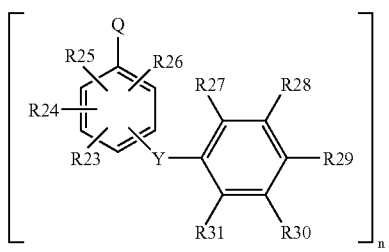

(wherein Q represents a chlorine atom, bromine atom, or iodine atom;

Y represents an oxygen atom, sulfur atom, —C(R32)(R33)-, —N(R34)-, or arylene group; R18 to R34 each represent a hydrogen atom, alkyl group, alkenyl group, alkynyl group, aryl group, alkoxy group, aryloxy group, di-substituted amino group, heterocycle residue, or halogen atom, provided that any two bondable groups in R18 to R22 or in R23 to R34 may form a ring; n represents 1 or 2; when n in general formula (4) is 2, any of R18 to R22 represents a connecting group and the two moieties connected to each other may be the same or different; and when n in general formula (5) is 2, any of R23 to R34 represents a connecting group and the two moieties connected to each other may be the same or different).

2. The process for producing an arylamine as described under 1. above, wherein the aromatic halogen compound is an iodized compound or brominated compound.

3. The process for producing an arylamine as described under 1. above, wherein the at least one organic salt is selected from the group consisting of pyridinium salts, imidazolium salts, phosphonium salts, arsonium salts, and stibonium salts.

4. The process for producing an arylamine as described under 1. above, wherein the at least one organic salt is a phosphonium salts.

5. The process for producing an arylamine as described under 1. above, wherein the copper catalyst is used in an amount of 0.001 to 0.3 mol per mol of the aromatic halogen compound.

6. The process for producing an arylamine as described under 1. above, wherein the organic salt is used in an amount of 0.05 to 5.00 times by mole the amount of the copper catalyst.

7. The process for producing an arylamine as described under 1. above, wherein the organic salt is used in an amount of 0.60 to 1.20 times by mole the amount of the copper catalyst.

8. The process for producing an arylamine as described under 1. above, wherein the reaction temperature is 80 to 250° C.

9. The process for producing an arylamine as described under 1. above, wherein compound(s) selected from aromatic hydrocarbon compounds, saturated aliphatic compounds, unsaturated aliphatic compounds, saturated alicyclic compounds, and unsaturated alicyclic compounds are used as reaction solvents.

10. The process for producing an arylamine as described under 9 above, wherein at least one of the reaction solvents to be used is an aromatic hydrocarbon compound or an unsaturated alicyclic compound.

BRIEF DESCRIPTION OF DRAWINGS

The above objects will become easily understood by one of ordinary skill in the art when the following detailed description is read in connection with the accompanying drawings.

BEST MODE FOR CARRYING OUT THE INVENTION

Figure 1:
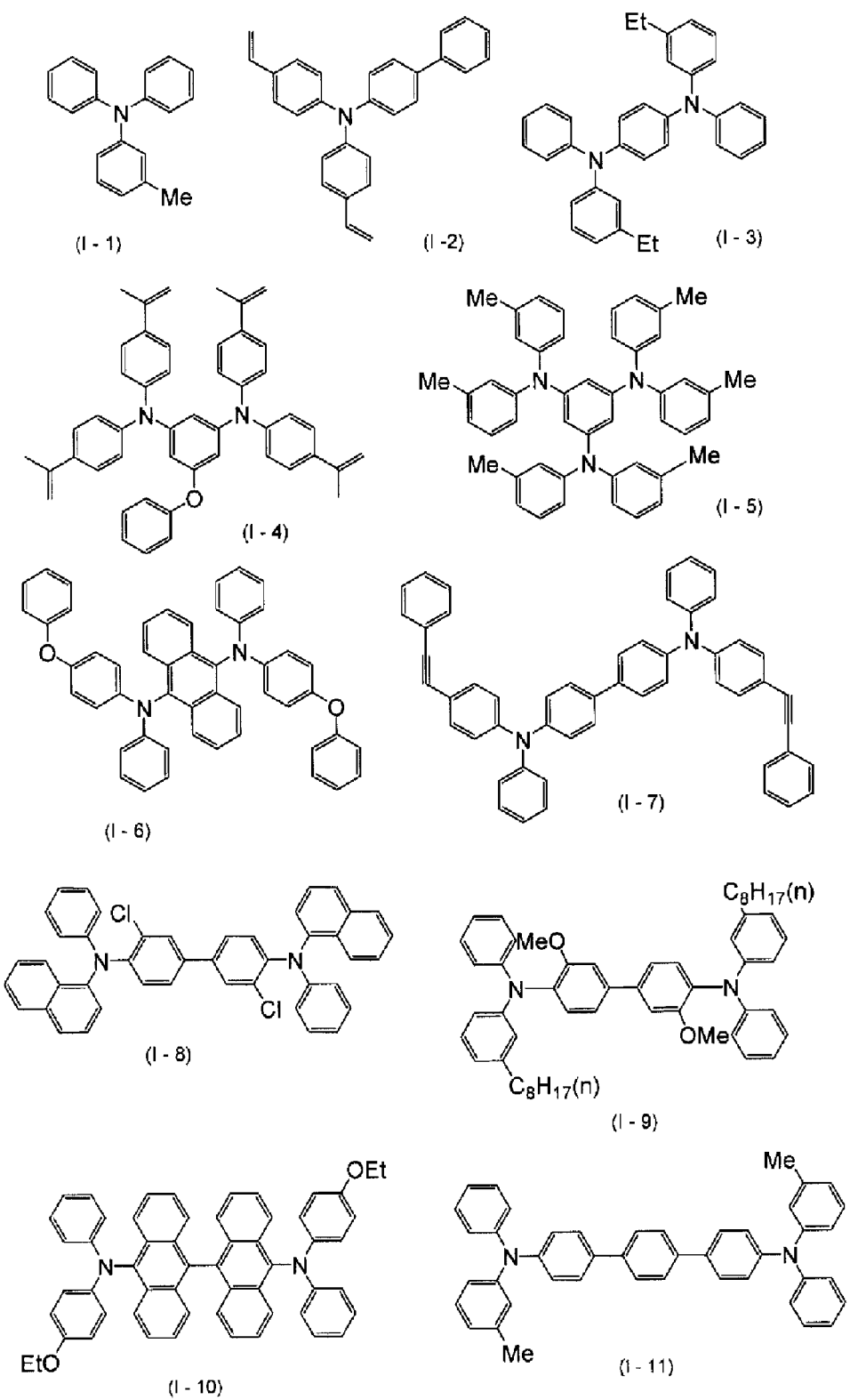
FIG. 1 contains structural formulas corresponding to the arylamines of Examples I-1 to I-11.

The invention will be explained in more detail.

The invention is a novel production process in which an arylamine, in particular any of a group of triarylamines or diarylamines useful as raw materials for electronic materials or as intermediates therefor, is produced by using the Ullmann condensation reaction, and which is characterized in that this reaction is conducted in the presence of a copper catalyst, a base, and the organic salt. In the process of the invention, due to the presence of the organic salt, even a substrate substituted by an inactive group can be reacted at lower temperatures than in the techniques of the Ullmann reaction which have been used hitherto and, hence, a high-purity arylamine compound can be produced therefrom. Furthermore, it is possible to use chlorinated aromatic compounds and brominated aromatic compounds, use of which has been difficult in the techniques of the Ullmann reaction heretofore in use. High-purity arylamine compounds can hence be produced at low cost.

The organic salts usable in the invention are compounds represented by general formulae (1) to (3). These compounds can be used alone or in combination of two or more thereof.

In the compounds represented by general formulae (1) to (3), examples of R1 to R17 include a hydrogen atom; linear alkyl groups such as methyl, trifluoromethyl, hexyl, dodecyl, hexadecyl, and octadecyl; branched alkyl groups such as isopropyl and t-butyl; cyclic alkyl groups such as cyclopentyl, cyclohexyl, and adamantly; alkenyl groups such as vinyl, allyl, isopropenyl, styryl, and cinnamyl; alkynyl groups such as ethynyl, 1-propynyl, 1-butynyl, phenylethynyl, mesityl-1-propynyl, and naphthyl-1-butynyl; aryl groups such as phenyl, tolyl, and naphthyl; hydroxyl; alkoxy groups such as methoxy, ethoxy, propoxy, isopropoxy, and t-butoxy; aryloxy groups such as phenoxy and naphthyloxy; mercapto; alkylthio groups such as ethylthio, n-hexylthio, and isotetradecylthio; arylthio groups such as phenylthio and naphthylthio; carbonyl groups such as acetyl, n-hexylcarbonyl, benzoyl, naphthoyl, and carbamoyl; sulfonyl groups such as methylsulfonyl, isopropylsulfonyl, phenylsulfonyl, and sulfamoyl; oxycarbonyl groups such as methoxycarbonyl, 1-octyloxycarbonyl, and phenoxycarbonyl; carbonyloxy groups such as acetyloxy, n-octylcarbonyloxy, and benzoyloxy; nitro; cyano; amino groups such as amino, methylamino, ethylamino, n-hexylamino, phenylamino, N,N-dimethylamino, N,N-dioctylamino, N,N-diphenylamino, and N-ethyl-N-phenylamino; carbonylamino groups such as acetylamino, tert-butylcarbonylamino, and benzoylamino; sulfonylamino groups such as ethylsulfonylamino, n-dodecylsulfonylamino, and phenylsulfonylamino; heterocycle residues such as 2-furyl, 2-thienyl, and 2-pyridyl; and halogen atoms such as fluorine, chlorine, bromine, and iodine. These groups may further have substituents. The substituents are not particularly limited as long as they do not participate in the reaction, and examples thereof include the substituents represented by the R1 to R17 described above.

Two bondable substituents in R1 to R6 or in R7 to R13 may be bonded to each other to form a ring. Examples of the ring include saturated rings such as cyclobutane, cyclopentane, and cyclohexane; partly saturated rings such as cyclobutene, cyclopentene, and cyclohexene; aromatic rings such as benzene and naphthalene; and heterocycles such as pyrrolidine, piperidine, pyrrole, and pyridine. These rings may further have substituents, and may have a ring fused thereto. In the case where these rings further have substituents, the substituents are not particularly limited as long as they do not participate in the reaction. Examples of the substituents include the substituents represented by the R1 to R17 described above.

Symbol m represents 1 or 2. When m=2, any of R2 to R6 represents a connecting group and the two moieties connected to each other may be the same or different.

$X^-$ is any desired anion. This anion is not particularly limited as long as it can make the organic salt stable. Examples of $X^-$ include halogen ions such as $F^-$, $Cl^-$, $Br^-$, and $I^-$; hydroxide ion; oxoacid ions such as $ClO^-$, $ClO_2^-$, $ClO_3^-$, $ClO_4^-$, $BrO^-$, $BrO_2^-$, $BrO_3^-$, $BrO_4^-$, $IO^-$, $IO_2^-$, $IO_3^-$, $IO_4^-$, $HCO_3^-$, $HSO_4^-$, $NO_2^-$, $NO_3^-$, $BO_2^-$, $BO_3^-$, $H_2PO_2^-$, $H_2PO_3^-$, and $H_2PO_4^-$; polyhalogen ions such as $ClI_2^-$, $ClBr_2^-$, $BrCl_2^-$, $BrI_2^-$, $ICl_2^-$, $IBr_2^-$, $Br_3^-$, and $I_3^-$; carboxylic acid ions such as $CH_3CO_2^-$, $CF_3CO_2^-$, and $n\text{-}C_3F_7CO_2^-$; sulfonic acid ions such as $CH_3SO_3^-$, $CF_3SO_3^-$, $n\text{-}C_4F_9SO_3^-$, and $CH_3C_6H_4SO_3^-$; imide ions such as $N(CF_3SO_2)_2^-$; carbonium ions such as $C(CF_3SO_2)_3^-$; boric acid ions such as $BF_4^-$, $B(C_6H_5)_4^-$, and $B_5O_8^-$; hydrofluoric acid ions such as $HF_2^-$ and $H_2F_3^-$; phosphoric acid ions such as $PF_6^-$; thiocyanic acid ions such as $SCN^-$ and $NCS^-$; and antimonide ions such as $SbF_6^-$ and $SbCl_6^-$.

Examples of the organic salts represented by general formula (1) include the following.

(i) Pyridinium salts: 1-ethylpyridinium chloride, 1-n-butylpyridinium chloride, 1-hexylpyridinium chloride, 1-acetonylpyridinium chloride, 4-carbamoyl-1-n-hexadecylpyridinium chloride, 1-(carbamoylmethyl)pyridinium chloride, 3-carbamoyl-1-methylpyridinium chloride, 1-cyanomethylpyridinium chloride, 4-dimethylamino-1-neopentylpyridinium chloride, 1-(ethoxycarbonylmethyl) pyridinium chloride, 1-methylpyridinium-2-aldoxime chloride, N-n-octadecyl-4-stilbazole bromide, 1-aminopyridinium iodide, 2-chloro-1-methylpyridinium iodide, 1-ethoxy-4-methoxycarbonylpyridinium iodide, 1-n-hexylpyridinium tetrafluoroborate, 2-bromo-1-ethylpyridinium tetrafluoroborate, 1-fluoro-3,5-dichloropyridinium tetrafluoroborate, 1-fluoro-2,4,6-trimethylpyridinium tetrafluoroborate, 1-butylpyridinium hexafluorophosphate, 2-chloro-1-methylpyridinium p-toluenesulfonate, 1-fluoro-3,5-dichloropyridinium triflate, 1-fluoro-2,4,6-trimethylpyridinium triflate, and the like.

(ii) Bipyridinium salts: 1,1'-dimethyl-2,2'-bipyridinium dichloride, 1,1'-dimethyl-2,3-bipyridinium dichloride, 1,1'-diethyl-2,4-bipyridinium dichloride, 1,1'-dibenzyl-4,4'-bipyridinium dichloride, 1,1'-n-butyl-2,3-bipyridinium dibromide, 1,1'-dipentyl-2,4-bipyridinium dibromide, 1,1'-diphenyl-4,4'-bipyridinium dibromide, 1,1'-bis(2,4-dinitrophenyl)-4,4'-bipyridinium dibromide, 1,1'-di-n-hexyl-2,2-bipyridinium diiodide, 1,1'-di-n-octyl-2,3-bipyridinium diiodide, 1,1'-diphenyl-4,4'-bipyridinium diiodide, and the like.

(iii) Quinolinium salts: 1-n-propylquinolinium chloride, 1-phenylquinolinium chloride, 1-ethylisoquinolinium bromide, 1-benzylisoquinolinium bromide, 1-isopropylbenzo[b]quinolinium bromide, 1-n-butylbenzo[f]quinolinium bromide, 1-isobutylbenzo[g]quinolinium bromide, 1-sec-butylbenzo[h]quinolinium bromide, 1-t-butylbenzo[c]isoquinolinium iodide, 1-n-decylbenzo[c]isoquinolinium iodide, and the like.

Examples of the organic salts represented by general formula (2) include the following.

(i) Imidazolium salts: 1-ethyl-3-methylimidazolium chloride, 1-butyl-3-methylimidazolium chloride, 1-hexyl-3- methylimidazolium chloride, 1-butyl-2,3-dimethylimidazolium chloride, 1,3-didecyl-2-methylimidazolium chloride, 2-chloro-1,3-dimethylimidazolium chloride, 1-dodecyl-2-methyl-3-benzylimidazolium chloride, 1,3-bis(2,6-isopropylphenyl)imidazolium chloride, 1,3-bis(2,4,6-trimethylphenyl)imidazolium chloride, 1,3,4,5-tetraphenylimidazolium bromide, 1,3-dicyclohexylimidazolium iodide, 1,3-diadamantylimidazolium iodide, 2,4,5-trichloro-1,3-dimethylimidazolium tetrafluoroborate, 1-hexyl-3-methylimidazolium hexafluorophosphate, 1-ethyl-3-methylimidazolium trifluoromethanesulfonate, and the like.

(ii) Imidazolinium salts: 1,3-dimethylimidazolinium chloride, 2-chloro-1,3-dimethylimidazolinium chloride, 2-chloro-1,3-diethylimidazolinium chloride, 1,3-diethylimidazolinium bromide, 1,3-di-n-butylimidazolinium bromide, 2,4,5-trichloro-1,3-dimethylimidazolinium p-toluenesulfonate, 2-chloro-4,5-diphenyl-1,3-dimethylimidazolinium tetrafluoroborate, 2-chloro-1,3-dimethylimidazolinium hexafluorophosphate, 2-chloro-1,3-dimethylimidazolinium trifluoromethanesulfonate, and the like.

(iii) Benzimidazolium salts: 1,3-dimethylbenzimidazolium chloride, 1-ethyl-3-methylbenzimidazolium chloride, 1-butyl-3-methylbenzimidazolium bromide, 1-hexyl-3-methylbenzimidazolium bromide, 2-chloro-1,3-dimethylbenzimidazolium bromide, 1-butyl-2,3-dimethylbenzimidazolium iodide, 2-phenyl-1-hexyl-3-methylbenzimidazolium iodide, and the like.

Examples of the organic salts represented by general formula (3) include the following.

(i) Ammonium salts: tetraethylammoniumfluoride, trimethylstyrylammonium chloride, tetra-n-butylammonium chloride, tetra-n-amylammonium chloride, benzyltriethylammonium chloride, trimethylvinylammonium bromide, 3-(trifluoromethyl)phenyltrimethylammonium bromide, tetra-n-hexylammonium bromide, benzyltriethylammonium iodide, N,N-dimethylmethyleneammonium iodide, (2-hydroxyethyl)triethylammonium iodide, 3-(trifluoromethyl)phenyltrimethylammonium iodide, benzyltriethylammonium hydroxide, benzyltrimethylammonium tribromide, n-hexadecyltrimethylammonium hexafluorophosphate, n-hexadecyltrimethylammonium perchlorate, n-hexadecyltrimethylammonium tetrafluoroborate, tetra-n-butylammonium difluoride, tetra-n-butylammonium dibromochloride, tetra-n-butylammonium dibromoiodide, tetra-n-butylammonium dihydrogen trifluoride, tetra-n-butylammonium hexafluorophosphate, tetra-n-butylammoniumhydrogensulfate, tetra-n-butylammonium perchlorate, tetra-n-butylammonium phosphate, tetra-n-butylammonium tetraphenylborate, tetra-n-butylammonium thiocyanate, tetra-n-butylammonium triiodide, tetraethylammonium p-toluenesulfonate, tetraethylammonium trifluoromethanesulfonate, tetramethylammonium acetate, tetramethylammonium sulfate, acetylcholine bromide, benzoylthiocholine iodide, and the like.

(ii) Phosphonium salts: tetra-n-butylphosphonium fluoride, acetonyltriphenylphosphonium chloride, allyltriphenylphosphonium chloride, benzyltriphenylphosphonium chloride, 4-chlorobenzyltriphenylphosphonium chloride, 4-chloromethyltriphenylphosphonium chloride, cyanomethyltri-n-butylphosphonium chloride, methoxymethyltriphenylphosphonium chloride, tetra-n-butylphosphonium chloride, tetrakis(hydroxymethyl)phosphonium chloride, tetraphenylphosphonium chloride, (formylmethyl)phosphonium chloride, methoxycarbonylmethyl(triphenyl)phosphonium chloride, allyltriphenylphosphonium bromide, n-amyltriphenylphosphonium bromide, benzyltriphenylphosphonium bromide, bromomethyltriphenylphosphonium bromide, 3-bromopropyltriphenylphosphonium bromide, n-butyltriphenylphosphonium bromide, 2-carboxyethyltriphenylphosphonium bromide, 4-carboxybutyltriphenylphosphonium bromide, 3-carboxypropyltriphenylphosphonium bromide, cinnamyltriphenylphosphonium bromide, cyclopropyltriphenylphosphonium bromide, 2-dimethylaminoethyltriphenylphosphonium bromide, 4-ethoxybenzyltriphenylphosphonium bromide, ethoxytriphenylphosphonium bromide, n-heptyltriphenylphosphonium bromide, n-hexyltriphenylphosphonium bromide, ethoxycarbonylmethyl(triphenyl)phosphonium bromide, methyltriphenylphosphonium bromide, ethyltriphenylphosphonium bromide, n-propyltriphenylphosphonium bromide, n-butyltriphenylphosphonium bromide, tetraethylphosphonium bromide, tetra-n-octylphosphonium bromide, tetraphenylphosphonium bromide, triphenylvinylphosphonium bromide, phenacyltriphenylphosphonium bromide, isopropyltriphenylphosphonium iodide, (N-methyl-N-phenylamino)triphenylphosphonium iodide, methyltriphenylphosphonium iodide, tetraphenylphosphonium iodide, tetra-n-butylphosphonium hydroxide, tetraethylphosphonium hexafluorophosphate, tetraethylphosphonium tetrafluoroborate, tetrakis(hydroxymethyl)phosphonium sulfate, tetraphenylphosphonium tetraphenylborate, and the like.

(iii) Arsonium salts: tetra-n-butylarsonium chloride, tetra-n-butylarsoniumbromide, triphenylmethylarsonium iodide, triphenyl(2-methylphenyl)arsonium hydroxide, triphenyl(4-methoxyphenyl)arsonium acetate, triphenyl(4-chlorophenyl)arsonium nitrate, triphenyl(3-nitrophenyl)arsonium perchlorate, triphenyl(2,4,6-trimethylphenyl)arsonium tetrafluoroborate, tris(3-methylphenyl)(phenyl)arsonium tetraphenylborate, tris(4-methoxyphenyl)(phenyl)arsonium hexafluorophosphate, tris(4-fluorophenyl)(phenyl)arsonium trifluoromethanesulfonate, and the like.

(iv) Stibonium salts: tetra-n-butylstibonium bromide, tetraphenylstibonium bromide, triphenylmethylstibonium iodide, triphenylbenzylstibonium hydroxide, triphenyl(2-methylphenyl)stibonium perchlorate, triphenyl(4-methoxyphenyl)stibonium tetrafluoroborate, tris(4-methylphenyl)(methyl)stibonium hexafluorophosphate, tris(2-methoxyphenyl)(methyl)stibonium trifluoromethanecarbonate, tetrakis(4-methylphenyl)stibonium trifluoromethanesulfonate, and the like.

Those organic salts may be added as they are to the reaction system. Alternatively, any of those organic salts may be prepared in the reaction system by a known method (e.g., *Ann.*, 1851, 78, 95; *Ann.*, 1902, 321, 166; *Ber.*, 1915, 48, 1759; *Ber.*, 1921, 54, 1451, 1461; *J. Chem. Soc.*, 1930, 1921; *Ber.*, 1954, 61, 908; *Ann.*, 1952, 577, 26; *Inorg. Chem.*, 1971, 10, 1900; *Inorg. Chem.*, 1996, 35(5), 1168; *Chem. Eur. J.*, 1996, 12(2), 1627; *Ionics*, 1997, 3, 356; *Chem. Commun.*, 2001, 1466; etc.) and used as it is for the reaction. Organic salts bonded to a polymer, e.g., polystyrene, also are commercially available and can be used in the same manner. Use of this kind of organic salt is preferred because it can be recovered and reused.

By using any of those organic salts in conducting the Ullmann reaction in the presence thereof, the reaction can be carried out at lower temperatures. In addition, it is possible to use the chlorinated aromatic compounds and brominated aromatic compounds which have been difficult to use in the techniques used hitherto for synthesizing an arylamine by the Ullmann reaction.

Preferred of those organic salts are the phosphonium salts, arsonium salts, or stibonium salts. When these salts are added, a significant reaction-accelerating effect is obtained and a high-purity arylamine compound can be obtained in high yield. More preferred salts among these include tetra-n-butylphosphonium chloride, benzyltriphenylphosphonium chloride, tetraphenylphosphonium chloride, tetra-n-butylphosphonium bromide, tetraphenylphosphonium bromide, methyltriphenylphosphonium bromide, ethyltriphenylphosphonium bromide, n-butyltriphenylphosphonium bromide, tetra-n-butylphosphonium hydroxide, tetra-n-butylarsonium chloride, tetra-n-butylarsonium bromide, triphenylmethylarsonium iodide, triphenyl(2-methylphenyl)arsonium hydroxide, triphenyl(2,4,6-trimethylphenyl)arsonium tetrafluoroborate, tris(3-methylphenyl)(phenyl)arsonium tetraphenylborate, tetra-n-butylstibonium bromide, tetraphenylstibonium bromide, triphenylmethylstibonium iodide, triphenylbenzylstibonium hydroxide, triphenyl(2-methylphenyl)stibonium perchlorate, and tris(4-methylphenyl)(methyl)stibonium hexafluorophosphate. Especially preferred of these are the phosphonium salts because they are more inexpensive and less toxic.

Those organic salts are used in an amount in the range of 0.05-5.00 times by mole the amount of the copper catalyst contained (in such a proportion that the organic-salt amount is 0.05-5.00 mol per mol of the copper catalyst). The amount of the organic salts to be used is preferably in the range of 0.40-2.00 times by mole, more preferably in the range of 0.60-1.20 times by mole. By using the organic salts in an amount regulated so as to be within that range, a sufficient reaction-accelerating effect is obtained and a decrease in reaction rate and an increase in impurity amount are inhibited. That range is hence preferred.

The aromatic halogen compound to be used in the invention is a compound represented by general formula (4) or (5).

in general formula (4) or (5), Q represents a chlorine atom, bromine atom, or iodine atom. Y represents an oxygen atom, sulfur atom, —C(R32)(R33), —N(R34), or arylene group. When Y is an arylene group, examples thereof include phenylene, naphthylene, anthranylene, phenanthrylene, and pyrenylene. R18 to R34 specifically represents a hydrogen atom; a linear alkyl group such as methyl, trifluoromethyl, hexyl, dodecyl, hexadecyl, or octadecyl; a branched alkyl group such as isopropyl or t-butyl; a cyclic alkyl group such as cyclopentyl, cyclohexyl, or adamantly; an alkenyl group such as vinyl, allyl, isopropenyl, styryl, or cinnamyl; an alkynyl group such as ethynyl, 1-propynyl, 1-butynyl, phenylethynyl, mesityl-1-propynyl, or naphthyl-1-butynyl; an aryl group such as phenyl, mesityl, biphenyl, naphthyl, or phenanthryl; an alkoxy group such as methoxy, propoxy, isopropoxy, or t-butoxy; an aryloxy group such as phenoxy, tolyloxy, xylyloxy, or naphthyloxy; a di-substituted amino group such as dimethylamino, N-ethyl-N-phenylamino, diphenylamino, or N-phenyl-N-naphthylamino; a heterocycle residue such as furyl, thienyl, or pyridyl; or a halogen atom such as a fluorine atom, chlorine atom, bromine atom, or iodine atom. These groups may further have substituents. Examples of the substituents include the substituents represented by the R18 to R34 described above.

Any desired two bondable groups in R18 to R22 or in R23 to R34 may form a ring. Examples of the ring thus formed include saturated rings such as cyclopentane, cyclohexane, cycloheptane, and adamantane; unsaturated rings such as cyclopentadiene, benzene, cycloheptene, and cycloheptatriene; and heterocycles such as oxolane, thiolane, oxane, thiane, and N-substituted piperidines. These rings may further have substituents, and may have a ring fused thereto. In the case where these rings further have substituents, the substituents are not particularly limited as long as they do not participate in the reaction. Examples of the substituents include the substituents represented by the R18 to R34 described above.

Symbol n represents 1 or 2. When n in general formula (4) is 2, any of R18 to R22 represents a connecting group and the two moieties connected to each other may be the same or different. When n in general formula (5) is 2, any of R23 to R34 represents a connecting group and the two moieties connected to each other may be the same or different.

In the case of an aromatic halogen compound substituted by an electron-attracting group such as a nitro, cyano, or carboxyl group, it shows higher reactivity. Consequently, even a chlorinated aromatic compound or brominated aromatic compound has been able to be used, and it has been possible to conduct the reaction at a lower reaction temperature than in the related-art techniques of the Ullmann reaction. However, in the case where an aromatic halogen compound which is unsubstituted or has been substituted by an electron-donating group is used as a substrate, it shows low reactivity and the reaction usually necessitates a high temperature and a prolonged period. The substrate to be used in the invention is an aromatic halogen compound which is unsubstituted or has been substituted by an electron-donating group. By using the invention, the arylamines the synthesis of which has been possible only under exceedingly severe conditions can be synthesized under mild reaction conditions. Furthermore, according to the invention, it is also possible to use the more inexpensive chlorinated aromatic compounds or brominated aromatic compounds which have been difficult to use in the related-art techniques of the Ullmann reaction.

The aromatic amine to be used as a starting material in the invention is a compound represented by the following general formula (6) or (7).

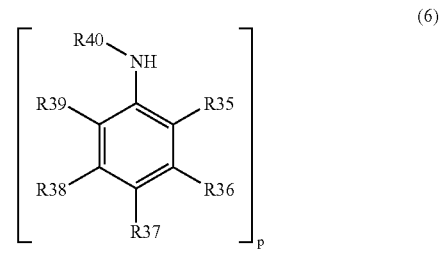

(6)

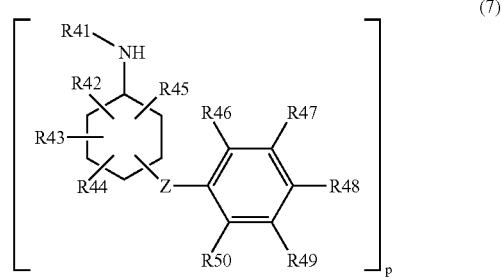

(7)

In the formulae, Z represents an oxygen atom, sulfur atom, —C(R51)(R52), —N(R53), or aryl group. R35 to R53 each represent a hydrogen atom, alkyl group, alkenyl group, alkynyl group, aryl group, alkoxy group, aryloxy group, amino group, nitro group, or heterocycle residue. Any desired two bondable groups in R35 to R40 or in R41 to R53 may form a ring. Symbol p represents 1 or 2. When p=2 in general formula (6), any of R35 to R40 represents a connecting group and the moieties connected to each other may be the same or different. When p=2 in general formula (7), any of R41 to R53 represents a connecting group and the two moieties connected to each other may be the same or different.

Examples of R35 to R53 include a hydrogen atom; linear alkyl groups such as methyl, trifluoromethyl, hexyl, dodecyl, hexadecyl, and octadecyl; branched alkyl groups such as isopropyl and t-butyl; cyclic alkyl groups such as cyclopentyl, cyclohexyl, and adamantly; alkenyl groups such as vinyl, allyl, isopropenyl, styryl, and cinnamyl; alkynyl groups such as ethynyl, 1-propynyl, and 1-butynyl; aryl groups such as phenyl, mesityl, biphenyl, naphthyl, and phenanthryl; alkoxy groups such as methoxy, propoxy, isopropoxy, and t-butoxy; aryloxy groups such as phenoxy, tolyloxy, xylyloxy, and naphthyloxy; amino groups such as amino, methylamino, n-hexylamino, phenylamino, dimethylamino, N-ethyl-N-phenylamino, and diphenylamino; nitro; and heterocycle residues such as furyl, thienyl, and pyridyl. These groups may further have substituents. In the case where the groups further have substituents, the substituents are not particularly limited as long as they do not participate in the reaction. Examples of the substituents include the substituents represented by the R35 to R53 described above.

In the case where Z is an arylene group, examples thereof include phenylene, naphthylene, anthranylene, phenanthrylene, and pyrenylene. This arylene group may be bonded in any desired position. Examples of the ring formed by two groups in R35 to R40 or in R41 to R53 include saturated rings such as cyclopentane, cyclohexane, cycloheptane, and adamantane; unsaturated rings such as cyclopentadiene, benzene, cycloheptene, and cycloheptatriene; and heterocycles such as pyrrolidine, pyrrole, piperidine, pyridine, morpholine, thiomorpholine, piperazine, azacycloheptane, azacycloheptene, and azacycloheptatriene. These rings may further have substituents and may have a ring fused thereto. In the case where the rings further have substituents, the substituents are not particularly limited as long as they do not participate in the reaction. Examples of the substituents include the substituents represented by the R35 to R53 described above. The amount of the aromatic amine compound to be used is generally 0.4-4 equivalents, preferably 0.5-2 equivalents, to the aromatic halogen compound.

The copper catalyst to be used in the invention is not particularly limited, and catalysts in ordinary use in the Ullmann condensation reaction can be used. Examples thereof include a copper powder, copper-(I) chloride, copper-(II) chloride, copper-(I) bromide, copper-(II) bromide, copper iodide, copper-(I) oxide, copper-(II) oxide, copper sulfate, copper nitrate, copper carbonate, and copper-(II) hydroxide. Preferred are the copper chlorides, copper bromides, and copper iodide. The amount of these copper catalysts to be used is generally 0.001-0.3 mol, preferably 0.01-0.2 mol, per mol of the aromatic halogen compound.

A promoter such as lithium iodide, sodium iodide, potassium iodide, rubidium iodide, or cesium iodide may be added according to need. In the case where these promoters are added, they are used in an amount of 0.001-0.5 mol, preferably 0.01-0.2 mol, per mol of the aromatic halogen compound.

Examples of the base to be used in the invention include alkali metal hydroxides such as lithium hydroxide, sodium hydroxide, potassium hydroxide, rubidium hydroxide, and cesium hydroxide, alkali metal carbonates such as lithium carbonate, sodium carbonate, potassium carbonate, rubidium carbonate, and cesium carbonate, alkali metal phosphates such as trilithium phosphate, trisodium phosphate, and tripotassium phosphate, and alkali metal alkoxides such as sodium methoxide, sodium ethoxide, potassium methoxide, potassium ethoxide, lithium tert-butoxide, sodium tert-butoxide, and potassium tert-butoxide. Of these bases, the alkali metal alkoxides may be added as they are to the reaction system or may be prepared from the alkali metals, alkali metal hydrides, alkali metal hydroxides, or the like and an alcohol and used. Preferred of these bases are sodium hydroxide, potassium hydroxide, sodium carbonate, and potassium carbonate.

These bases are used in an amount of 1.0-4.0 equivalents, preferably 1.2-2.0 equivalents, to the aromatic amine.

In the process of the invention, a reaction solvent need not be used. It is, however, possible to use an aromatic compound or aliphatic compound as a reaction solvent according to need. Examples thereof include the following solvents.

(I) Optionally halogenated aromatic hydrocarbon compounds: toluene, xylene, mesitylene, durene, ethylbenzene, diethylbenzene, isopropylbenzene, diisopropylbenzene, diphenylmethane, chlorobenzene, 1,2-dichlorobenzene, 1,2,4-trichlorobenzene, and the like.

(II) Hydrogenated aromatic hydrocarbon compounds having a partly hydrogenated ring framework such as a dihydro-, tetrahydro-, hexahydro-, octahydro-, or decahydro-framework: 1,4-dihydronaphthalene, 1,2,3,4-tetrahydronaphthalene, 9,10-dihydroanthracene, 9,10-dihydrophenanthrene, 4,5,9,10-tetrahydropyrene, 1,2,3,6,7,8-hexahydropyrene, dodecahydrotriphenylene, and the like.

(III) Saturated aliphatic compounds: heptane, octane, nonane, decane, undecane, dodecane, tridecane, 2-methyldodecane, 4-ethylundecane, tetradecane, pentadecane, 3,3-dimethyltridecane, hexadecane, heptadecane, 2-methyl-4-ethyltetradecane, and the like.

(IV) Unsaturated aliphatic compounds: 1-heptene, 2-heptyne, 2-octene, 3-nonene, 1-decyne, 1-undecene, 4-dodecene, 3,3-dimethyl-1-decene, 1,3,5-dodecatriene, 5-tridecene, 3-methyl-4-ethyl-2-decene, 1-dodecyne, 3-dodecene-1-yne, 1-tridecyne, 5,5-dimethyl-3-undecene-1-yne, 5-ethynyl-1,3-dodecadiene, ocimene, myrcene, squalene, and the like.

(V) Saturated alicyclic compounds: dicyclohexyl, decahydronaphthalene, dodecahydrofluorene, and the like.

(VI) Unsaturated alicyclic compounds: α-terpinene, β-terpinene, γ-terpinene, terpinolene, (+)-α-phellandrene, (−)-β-phellandrene, (−)-1-p-menthene, (+)-3-menthene, dipentene, (+)-limonene, (+)-sabinene, (+)-α-pinene, (+)-β-pinene, (−)-β-cadinene, (−)-β-caryophyllene, (−)-β-santalene, (−)-α-cedrene, (+)-β-selinene, (−)-β-bisabolene, α-humulene, and the like.

Preferred of these solvents are alkylbenzenes such as toluene, xylene, diethylbenzene, and diisopropylbenzene and terpenes such as α-terpinene, β-terpinene, γ-terpinene, phellandrene, and terpinolene. Use of these solvents inhibits the generation of impurities and enables a high-purity arylamine to be produced in high yield.

Those aromatic compounds and aliphatic compounds can be used alone or in combination of two or more thereof as a solvent. The reaction solvent may be used generally in an amount of 100-1,000 mL per mol of the aromatic halogen compound used as a starting material.

The reaction temperature in the invention is in the range of 80-250° C. In the case where the aromatic halogen compound to be used is an iodine compound, the reaction temperature is in the range of generally 80-180° C., preferably 90-130° C.

In the case of bromine compounds and chlorine compounds, the reaction temperature varies depending on the number of reaction sites. When these substrates each have one reaction site, the temperature is in the range of generally 80-250° C., preferably 90-130° C. When the substrates each have two or more reaction sites, the temperature is in the range of generally 80-250° C., preferably 170-210° C.

The reaction time varies depending on the starting materials to be used, organic salt to be added, and reaction conditions. However, in the case of aromatic iodine compounds, the reaction time is generally about 1-3 hours. In the case of aromatic chlorine compounds and aromatic bromine compounds, the reaction time is generally about 1-12 hours.

It is preferred that the reaction should be conducted in an inert gas atmosphere such as nitrogen or argon in order to prevent the generation of by-products and produce a high-purity arylamine.

Figure 2:
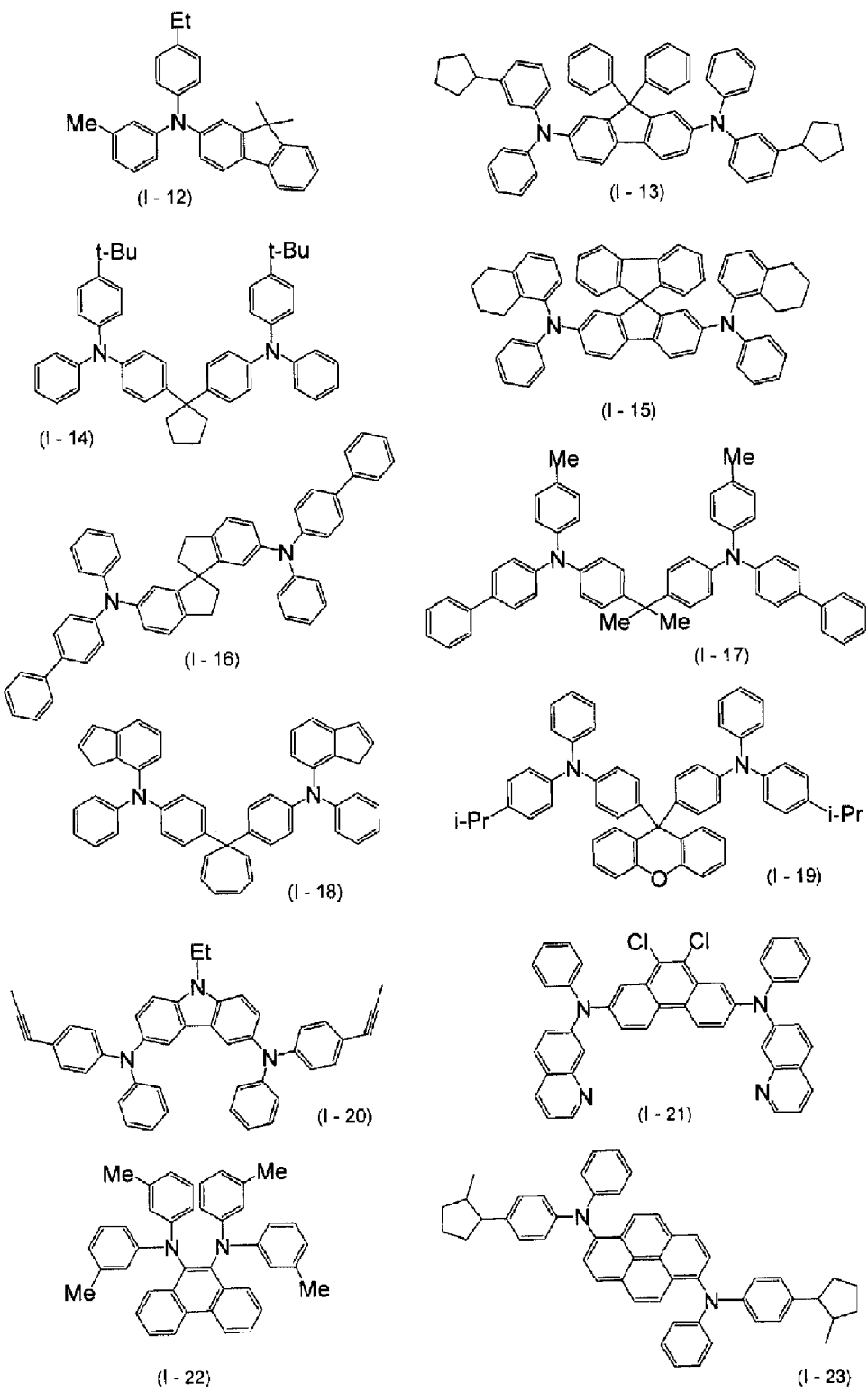
FIG. 2 contains structural formulas corresponding to the arylamines of Examples I-12 to I-23.
Figure 3:
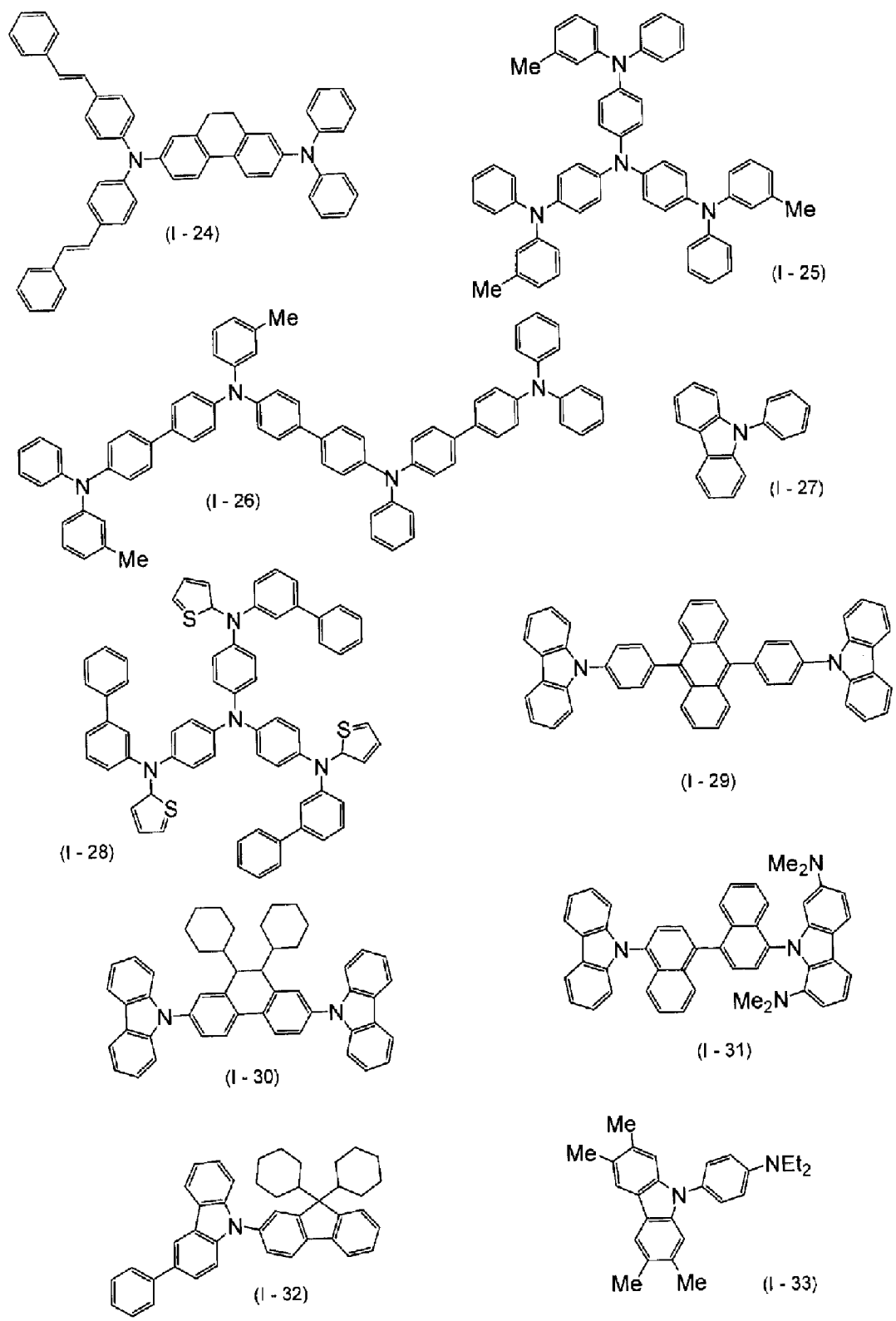
FIG. 3 contains structural formulas corresponding to the arylamines of Examples I-24 to I-33.
Figure 4:
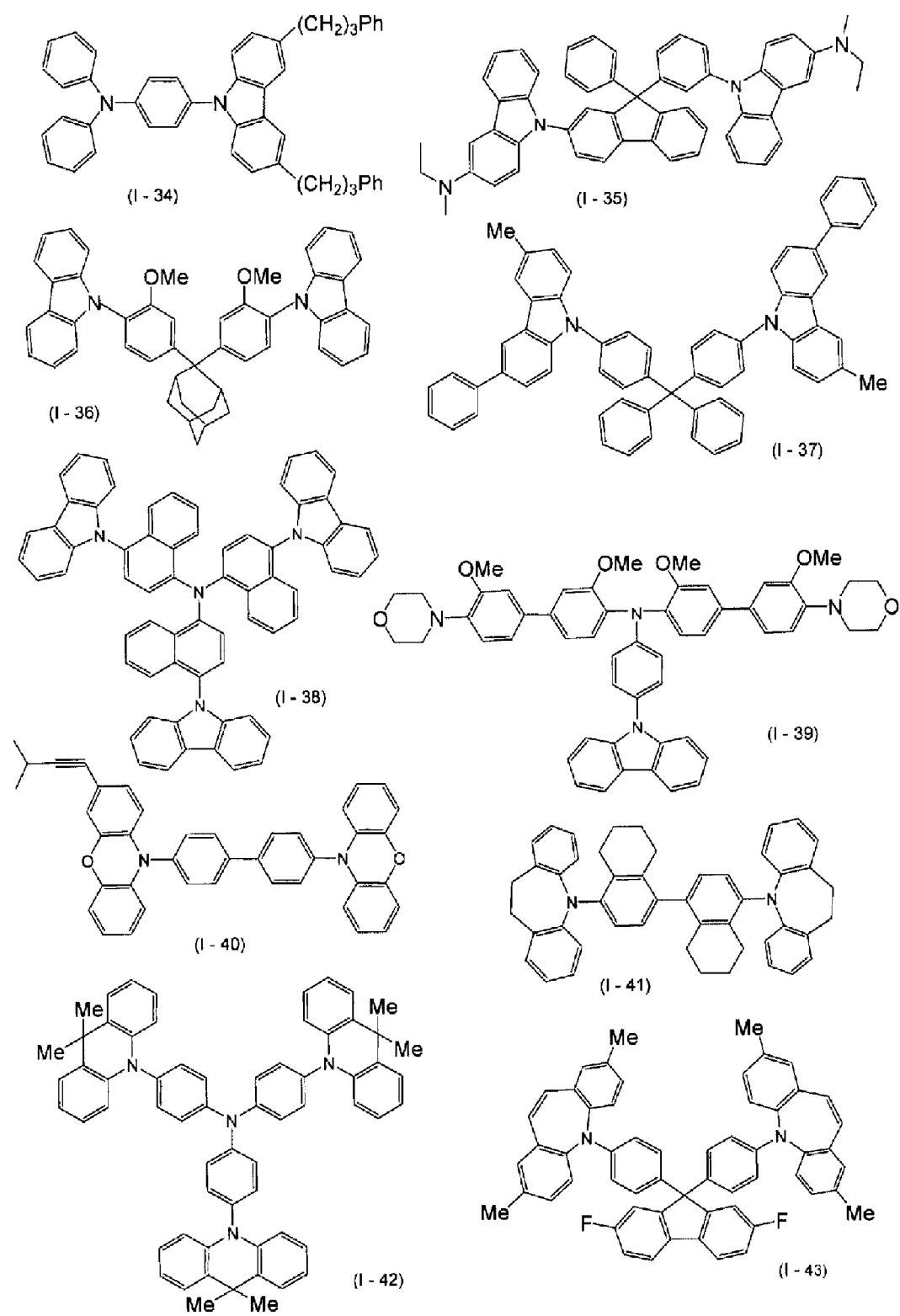
FIG. 4 contains structural formulas corresponding to the arylamines of Examples I-34 to I-43.
Figure 5:
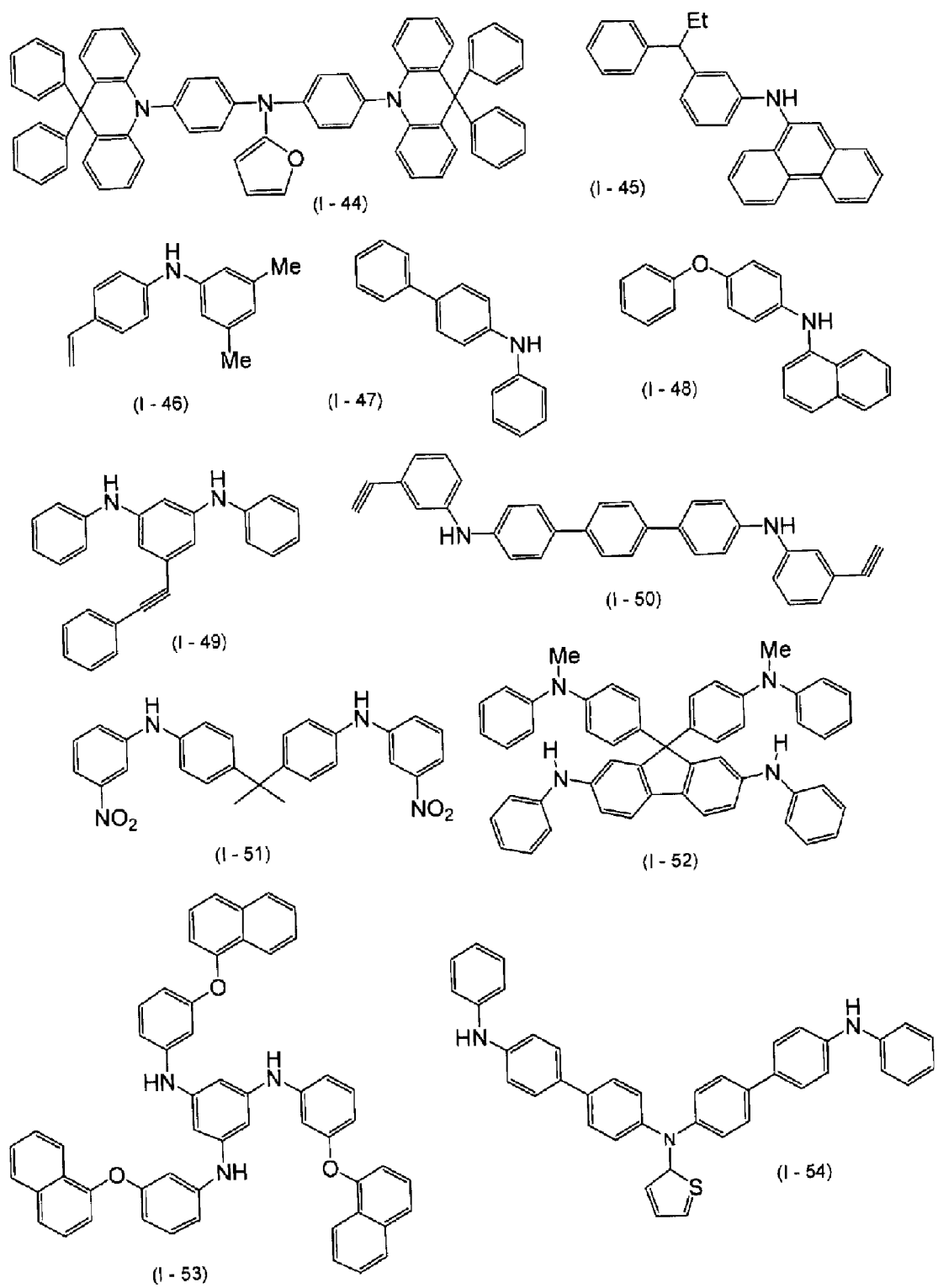
FIG. 5 contains structural formulas corresponding to the arylamines of Examples I-44 to I-54.

Specific examples of arylamines which can be synthesized by the invention are shown in FIGS. 1-5, but the arylamine to be produced by the invention should not be construed as being limited to these.

EXAMPLES

The invention will be explained below in more detail by reference to Examples, but the invention should not be construed as being limited to these. Incidentally, purity was evaluated by high-performance liquid chromatography (abbreviated as HPLC).

Example 1

Synthesis of N,N'-Diphenyl-N,N'-bis(3-methylphenyl)(p-terphenyl)-4,4"-diamine (exemplified compound I-11)

N-(3-Methylphenyl)-N-phenylamine was mixed in an amount of 18.05 g (98.52 mmol) with 11.87 g (24.63 mmol) of 4,4"-diiodo-1,1':4',1"-terphenyl, 11.06 g (197.0 mmol) of potassium hydroxide, 0.4 g (4.0 mmol) of copper-(I) chloride, 1.36 g (4.0 mmol) of tetra-n-butylphosphonium bromide, and 10 mL of toluene. This mixture was reacted at 115-125° C. for 1 hour in a nitrogen stream. After the reaction, 25 mL of toluene and 50 mL of water were added and the resultant mixture was subjected to liquid separation. Thereafter, the organic layer was washed with water and dehydrated and dried with anhydrous sodium sulfate. After the drying agent was removed by filtration, 3.9 g of activated clay was added. The resultant mixture was stirred at 50-55° C. for 1 hour and the clay was removed by filtration. The toluene was distilled off under reduced pressure and 28 mL of ethyl acetate was added to the residue. The resultant solution was cooled for crystallization, and the precipitate was taken out by filtration. Thus, the target compound (I-11) was obtained as white crude crystals in an amount of 13.7 g (yield, 94.0%). The target compound obtained had a melting point of 189-190° C. and a content as determined by HPLC of 99.5% (HPLC conditions: column, YMC-A-002; eluent, hexane/tetrahydrofuran (V/V=97/3); detection UV, 310 nm; flow rate, 0.8 mL/min).

Examples 2 to 8

Synthesis was conducted in the same manner as in Example 1, except that the aromatic halogen compound, organic salt, and base used in Example 1 were replaced by those shown in Table 1 and the reaction temperature was changed. The results obtained are shown in Table 1.

Comparative Examples 1 and 2

Synthesis was conducted in the same manner as in Example 1, except that no organic salt was used and the reaction temperature was changed to the temperature shown in Table 1. The results obtained are shown in Table 1.

Comparative Example 3

Synthesis was conducted in the same manner as in Example 1, except that the same aromatic halogen compound and base as in Example 8 were used and no organic salt was used. The results obtained are shown in Table 1.

TABLE 1

| | Organic salt | Aromatic halogen compound | Base | Reaction temperature (° C.) | Reaction time (hr) | Yield (%) | Purity (%) |
|---|---|---|---|---|---|---|---|
| Example 1 | tetra-n-butylphosphonium bromide | 4,4"-diiodo-1,1':4',1"-terphenyl | KOH | 115-125 | 1.0 | 94.0 | 99.5 |
| Example 2 | triphenylmethylarsonium iodide | 4,4"-diiodo-1,1':4',1"-terphenyl | KOH | 115-125 | 1.0 | 94.2 | 99.5 |
| Example 3 | tetraphenylstibonium bromide | 4,4"-diiodo-1,1':4',1"-terphenyl | KOH | 115-125 | 1.5 | 92.0 | 99.5 |
| Example 4 | benzyltriethylammonium chloride | 4,4"-diiodo-1,1':4',1"-terphenyl | KOH | 115-125 | 3.0 | 88.0 | 99.2 |
| Example 5 | n-butylpyridinium chloride | 4,4"-diiodo-1,1':4',1"-terphenyl | KOH | 115-125 | 3.0 | 84.6 | 98.7 |
| Example 6 | 1-ethyl-3-methylimidazolium chloride | 4,4"-diiodo-1,1':4',1"-terphenyl | KOH | 115-125 | 2.0 | 77.6 | 98.5 |
| Example 7 | triphenylmethylarsonium iodide | 4-chlorodiphenyl | KOH | 115-125 | 8.0 | 40.2 | 98.0 |
| Example 8 | tetraphenylphosphonium bromide | 4,4"-dibromo-1,1':4',1"-terphenyl | $K_2CO_3$ | 200-210 | 10.0 | 99.2 | 99.2 |

TABLE 1-continued

| | Organic salt | Aromatic halogen compound | Base | Reaction temperature (° C.) | Reaction time (hr) | Yield (%) | Purity (%) |
|---|---|---|---|---|---|---|---|
| Comparative Example 1 | none | 4,4''-diiodo-1,1':4',1''-terphenyl | KOH | 115-125 | >30 | — | — |
| Comparative Example 2 | none | 4,4''-diiodo-1,1':4',1''-terphenyl | KOH | 240-250 | 7.0 | 89.2 | 96.8 |
| Comparative Example 3 | none | 4,4''-dibromo-1,1':4',1''-terphenyl | $K_2CO_3$ | 200-210 | reaction did not proceed | — | — |

The results given in Table 1 show the following. In each of the Examples according to the invention, in which an organic salt was added, the reaction is completed at a lower reaction temperature or in a shorter time than in the Comparative Examples or completed at a lower temperature and a shorter time than in the Comparative Examples, and an arylamine having an exceedingly high purity can be synthesized in high yield. In contrast, in the Comparative Examples, in which no organic salt was added, the reaction does not proceed or proceeds only under high-temperature conditions. Furthermore, even in the case where a brominated aromatic compound which has been difficult to use in the related-art techniques of the Ullmann reaction is used, the target compound can be obtained in high yield by the process of the invention, in which the compound is reacted in the presence of an organic salt.

Example 9

Synthesis of N,N,N',N'-Tetra(3-methylphenyl)-9,10-diaminophenanthrene (exemplified compound I-22)

9,10-Bis(3-methylanilino)phenanthrene was mixed in an amount of 6.6 g (17.0 mmol) with 14.8 g (68.0 mmol) of m-iodotoluene, 3.82 g (68 mmol) of potassium hydroxide, 0.98 g (6.8 mmol) of copper-(I) bromide, 2.52 g (6.8 mmol) of ethyltriphenylphosphonium bromide, and 10 mL of terpinolene. This mixture was reacted at 115-125° C. for 2 hours in a nitrogen stream. After the reaction, the reaction solvent was distilled off by vacuum concentration. To the residue were added 5 mL of toluene, 67 mL of ethyl acetate, and 22 mL of water. The resultant mixture was subjected to liquid separation. To the organic layer was added 71 mL of methanol. The resultant solution was cooled for crystallization. Thus, the target compound (I-22) was obtained as light-yellow crude crystals in an amount of 9.0 g (yield, 93.0%). The target compound obtained had a melting point of 223-224° C. and a content as determined by HPLC of 99.6% (HPLC conditions: column, YMC-A-312; eluent, methanol/tetrahydrofuran (V/V=99/1); detection UV, 254 nm; flow rate, 1.0 mL/min).

Example 10

Synthesis of Tris{4-[N-(3-methylphenyl)-N-phenylamino]phenyl}amine (exemplified compound I-25)

Tris(4-bromophenyl)amine was mixed in an amount of 8.2 g (17.0 mmol) with 18.7 g (102.0 mmol) of N-(3-methylphenyl)-N-phenylamine, 13.5 g (102.0 mmol) of potassium carbonate, 0.5 g (2.6 mmol) of copper iodide, and 1.0 g (2.6 mmol) of benzyltriphenylphosphonium chloride. This mixture was reacted at 200-210° C. for 12 hours in a nitrogen stream. After the reaction, 100 mL of toluene and 50 mL of water were added and the resultant mixture was subjected to liquid separation. Thereafter, the organic layer was washed with water and dehydrated and dried with anhydrous sodium sulfate. After the drying agent was removed by filtration, 100 mL of hexane was added to the organic layer. The resultant solution was cooled for crystallization. Thus, the target compound (I-25) was obtained as light-yellow crude crystals in an amount of 7.9 g (yield, 85.3%). The target compound obtained had a melting point of 210-211° C. and a content as determined by HPLC of 99.2% (HPLC conditions: column, Super-ODS; eluent, methanol/tetrahydrofuran (V/V=97/3); buffer, triethylamine and acetic acid each in an amount of 0.1%; detection UV, 254 nm; flow rate, 0.8 mL/min).

Example 11

Synthesis of 9-Phenylcarbazole (exemplified compound I-27)

Carbazole was mixed in an amount of 16.47 g (98.52 mmol) with 31.0 g (197.04 mmol) of bromobenzene, 10.44 g (98.52 mmol) of sodium carbonate, 0.4 g (8.0 mmol) of copper-(I) chloride, and 3.0 g (8.0 mmol) of tetraphenylphosphonium chloride. This mixture was reacted at 115-125° C. for 2 hours in a nitrogen stream. After the reaction, 50 mL of toluene and 100 mL of water were added and the resultant mixture was subjected to liquid separation. Thereafter, the organic layer was washed with water and dried with anhydrous sodium sulfate. After the drying agent was removed by filtration, 15.6 g of activated clay was added. The resultant mixture was stirred at 50-55° C. for 1 hour and the clay was removed by filtration. The toluene was concentrated under reduced pressure and 352 mL of methanol was added to the residue. The resultant solution was subjected to crystallization. Thus, the target compound (I-27) was obtained as white crude crystals in an amount of 22.7 g (yield, 94.8%). The target compound obtained had a melting point of 96-97° C. and a content as determined by HPLC of 99.8% (HPLC conditions: column, ODS-80TM; eluent, acetonitrile/water (V/V=65/35); buffer, triethylamine and acetic acid each in an amount of 0.1%; detection UV, 254 nm; flow rate, 1.0 mL/min)

Examples 12 to 26

Compounds of Examples 12 to 26 were synthesized in the same manner. The results obtained are shown in Table 2.

TABLE 2

| Example No. | Aromatic halogen compound | Target compound No. | Organic salt | Base | Reaction temperature (° C.) | Reaction time (hr) | Yield (%) | Purity (%) |
| --- | --- | --- | --- | --- | --- | --- | --- | --- |
| 12 | m-bromotoluene | I-1 | methyltriphenylphosphonium bromide | NaOH | 100-110 | 4.0 | 84.2 | 98.2 |
| 13 | 1,3,5-trichlorobenzene | I-5 | tetra-n-butylstibonium bromide | $Na_3PO_4$ | 200-210 | 12.0 | 34.4 | 98.0 |
| 14 | 1-chloronaphthalene | I-8 | 1,3-dimethylimidazolinium chloride | NaOH | 120-130 | 9.0 | 39.0 | 98.2 |
| 15 | 9,9'-dichloro-10,10'-bianthracene | I-10 | tetra-n-butylphosphonium bromide | $Na_2CO_3$ | 180-190 | 10.0 | 37.6 | 98.0 |
| 16 | 2,7-dibromo-9,9-diphenylfluorene | I-13 | tetra-n-butylarsonium chloride | $K_2CO_3$ | 180-190 | 8.0 | 85.4 | 99.4 |
| 17 | 2,7-dibromospiro[9.9]-bifluorene | I-15 | triphenyl (2-methylphenyl)-stibonium perchlorate | NaOH | 170-180 | 6.5 | 87.6 | 99.5 |
| 18 | 2,7-dibromo-9,10-di-chlorophenanthrene | I-21 | tetra-n-butylphosphonium hydroxide | KOH | 170-180 | 6.0 | 78.3 | 99.4 |
| 19 | 9,10-bis (4-iodophenyl)-anthracene | I-29 | 1-butyl-2,3-dimethylimidazolium iodide | NaOH | 120-130 | 3.0 | 83.7 | 98.3 |
| 20 | 4,4'-diiodotetraphenyl-methane | I-37 | tris (3-methylphenyl) (phenyl)-arsonium tetraphenylborate | $Na_2CO_3$ | 95-105 | 4.0 | 91.3 | 99.3 |
| 21 | tris (4-bromonaphthyl)-amine | I-38 | n-butyltriphenylphosphonium bromide | NaOH | 110-120 | 9.0 | 86.9 | 99.0 |
| 22 | tris (4-iodophenyl) amine | I-42 | 1,1'-dimethyl-2,3-bipyridinium dichloride | $K_2CO_3$ | 120-130 | 3.5 | 79.9 | 98.6 |
| 23 | 9,9-bis (4-bromophenyl)-2,7-difluoro-9H-fluorene | I-43 | 1-phenylquinolinium chloride | $Na_2CO_3$ | 200-210 | 8.0 | 78.1 | 98.0 |
| 24 | 3,5-dimethylchlorobenzene | I-46 | triphenyl(2,4,6-trimethylphenyl)-arsonium tetrafluorobor | $K_3PO_4$ | 110-120 | 3.0 | 36.5 | 98.9 |
| 25 | 4-iodobiphenyl | I-47 | triphenylbenzylstibonium hydroxide | $Na_2CO_3$ | 110-120 | 2.0 | 92.8 | 99.4 |
| 26 | 1-bromonaphthalene | I-48 | tetra-n-butylarsonium chloride | NaOH | 120-130 | 2.0 | 92.7 | 99.3 |

INDUSTRIAL APPLICABILITY

According to the process of the invention, in which the Ullmann reaction is conducted in the presence of an organic salt represented by any of general formulae (1) to (3), an arylamine, especially a triarylamine or diarylamine, which is useful as a raw material for electronic materials or as an intermediate therefor can be produced at low cost. The process hence has exceedingly high suitability for practical use. In particular, even when chlorinated aromatic compounds or brominated aromatic compounds, which are more inexpensive, are used or when aromatic halogen compounds substituted by an electron-donating group, which do not efficiently reacted in the techniques of the Ullmann reaction heretofore in use, are used, arylamines having a high purity can be synthesized therefrom in high yield.

The invention claimed is:

1. A process for producing an arylamine, comprising reacting an aromatic halogen compound represented by the following general formula (4) or (5) with an aromatic amine in the presence of at least one organic salt represented by the following general formulae (1) to (3), a copper catalyst, and a base:

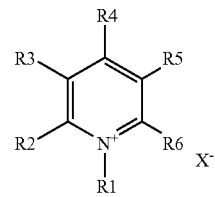

(1)

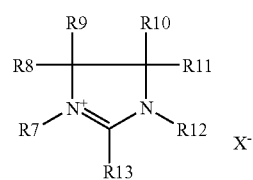

(2)

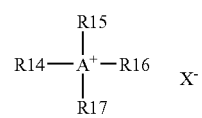

(3)

wherein A represents a nitrogen atom, phosphorus atom, arsenic atom, or antimony atom; R1 to R17 may be the same or different and each represents a hydrogen atom, alkyl group, alkenyl group, alkynyl group, aryl group, hydroxyl group, alkoxy group, aryloxy group, mercapto group, alkylthio group, arylthio group, carbonyl group, sulfonyl group, oxycarbonyl group, carbonyloxy group, nitro group, cyano group, amino group, carbonylamino group, sulfonylamino group, heterocycle residue, or halogen atom, provided that R1, R7, R12, and R14 to R17 each is not a hydrogen atom, that R8 and R10 in cooperation may form a double bond, and that two bondable substituents in R1 to R6 or in R7 to R13 may be bonded to each other to form a ring; and X⁻ represents any anion;

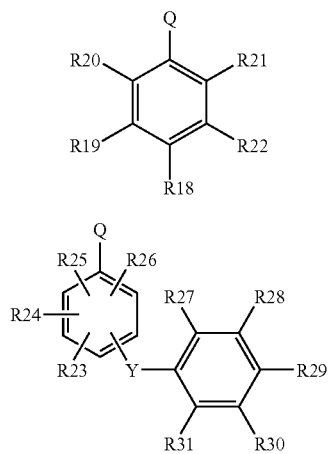

wherein Q represents a chlorine atom, bromine atom, or iodine atom; Y represents an oxygen atom, sulfur atom, —C(R32)(R33)-, —N(R34)-, or arylene group; and R18 to R34 each represents a hydrogen atom, alkyl group, alkenyl group, alkynyl group, aryl group, alkoxy group, aryloxy group, di-substituted amino group, heterocycle residue, or halogen atom, provided that any two bondable groups in R18 to R22 or in R23 to R34 may form a ring.

2. The process for producing an arylamine of claim 1, wherein the aromatic halogen compound is an iodized compound or brominated compound.

3. The process for producing an arylamine of claim 1, wherein the at least one organic salt is selected from the group consisting of pyridinium salts, imidazolium salts, phosphonium salts, arsonium salts, and stibonium salts.

4. The process for producing an arylamine of claim 1, wherein the at least one organic salt is a phosphonium salts.

5. The process for producing an arylamine of claim 1, wherein the copper catalyst is used in an amount of 0.001 to 0.3 mol per mol of the aromatic halogen compound.

6. The process for producing an arylamine of claim 1, wherein the organic salt is used in an amount of 0.05 to 5.00 times by mole the amount of the copper catalyst.

7. The process for producing an arylamine of claim 1, wherein the organic salt is used in an amount of 0.60 to 1.20 times by mole the amount of the copper catalyst.

8. The process for producing an arylamine of claim 1, wherein the reaction temperature is 80 to 250° C.

9. The process for producing an arylamine of claim 1, wherein compound(s) selected from aromatic hydrocarbon compounds, saturated aliphatic compounds, unsaturated aliphatic compounds, saturated alicyclic compounds, and unsaturated alicyclic compounds are used as reaction solvents.

10. The process for producing an arylamine of claim 9, wherein at least one of the reaction solvents to be used is an aromatic hydrocarbon compound or an unsaturated alicyclic compound.

* * * * *